United States Patent
van Scharrenburg et al.

(10) Patent No.: US 6,793,928 B1
(45) Date of Patent: Sep. 21, 2004

(54) VACCINES WITH AN LTB ADJUVANT

(75) Inventors: Gustaaf J. M. van Scharrenburg, Weesp (NL); Rudi Brands, Weesp (NL); Lolke de Haan, Weesp (NL); Willem Ronald Verweij, Weesp (NL); Jan C. Wilschut, Weesp (NL); Etienne Agsteribbe, deceased, late of Weesp (NL), legal representative Irene Agsteribbe-Servaas (73) Assignees: Duphar International Research BV, CP Weesp (NL); Universiteit Van Groningen, CP Groningen (NL)

(*) Notice: Subject to any disclaimer, the term of this patent is extended or adjusted under 35 U.S.C. 154(b) by 0 days.

(21) Appl. No.: 09/555,139

(22) PCT Filed: Nov. 24, 1998

(86) PCT No.: PCT/EP98/07553
§ 371 (c)(1),
(2), (4) Date: Dec. 13, 2000

(87) PCT Pub. No.: WO99/26654
PCT Pub. Date: Jun. 3, 2000

(30) Foreign Application Priority Data

Nov. 25, 1997 (NL) .......................................... 97203671

(51) Int. Cl.$^7$ ............................................ A61K 39/108
(52) U.S. Cl. .................... 424/257.1; 184/193.1; 184/197.11; 184/201.1; 184/209.1; 184/236.1; 184/241.1; 530/350; 435/69.1
(58) Field of Search ................ 435/69.1, 69.3, 435/69.7, 71.1; 530/350; 424/184.1, 193.1, 197.11, 200.1, 201.1, 209.1, 236.1, 241.1, 257.1

(56) References Cited
U.S. PATENT DOCUMENTS 5,182,109 A * 1/1993 Tamura et al.
5,241,053 A * 8/1993 Fujisawa et al. .............. 424/89

FOREIGN PATENT DOCUMENTS

| GB | 1 498 261 | | 1/1978 |
| WO | WO90 06366 | * | 6/1909 |
| WO | 90/06366 | * | 6/1990 |

OTHER PUBLICATIONS

Kikuta, et al, 1990, "Cross–protection against . . . ," Vaccine 8: 595–599, 1990.*
Nashar, et al, "Current progress in the development of . . . ," Vaccine 11(2):235–239, 1993.*
Smerdou, et al, "A continuous epitope from . . . ," Virus Research 41:1–9, 1996.*
Tamura et al, "Cross–protection against. . . ," Journal of Immunol. 149(3): 981–988, 1992.*
Fox, 1994, "No Winners Against AIDS", Biol Techn. 12:128, 1994.*
Feinberg, et al., "AIDS Vaccine Models . . . ," Nature Medicine 8(3):207–210, 2002.*
Haynes, et al, "Update On Issues Of HIV . . . ," Ann. Med. 28:39–41, 1996.*

(List continued on next page.)

*Primary Examiner*—Jennifer E. Graser
(74) *Attorney, Agent, or Firm*—Finnegan, Henderson, Farabow, Garrett & Dunner L.L.P.

(57) ABSTRACT

The present invention relates to a vaccine containing at least one particulate immunogen and an adjuvanting amount of B subunits of heat-labile enterotoxin characteristic of *E. Coli*. More in particular, this invention relates to vaccines wherein the adjuvanting LTB is free from contaminating A subunits or holotoxin. To this end, preferably, use is made of LTB prepared by recombinant DNA techniques. The particulate immunogens can relate to or can be derived from e.g. viruses, bacteria or fungi. This vaccine is particularly suitable for the induction of a protective response against said particulate immunogen upon mucosal (e.g. intra-nasal) administration. It was found that such administration results in both systemic and mucosal protection against the pathogen to which the particulate immunogen relates.

19 Claims, 8 Drawing Sheets

OTHER PUBLICATIONS

Hirabayashi et al., "Comparison of intransal inoculation of influenza HA vaccine combined with cholera toxin B subunit with oral or parenteral vaccination," *Vaccine* 8:243–248 (1990).

Kikuta et al., "Cross–protection against influenza B type virus infection by intranansal inoculation of the HA vaccines combined with cholera toxin B subunit," *Vaccine* 8:595–599 (1990).

Tamura et al., "Cross–Protection Against Influenza Virus Infection Afforded By Trivalent Inactivated Vaccines Inoculated Intranasally With Cholera Toxin B Subunit," *J. Immunology* 3:981–988 (1992).

Tamura et al., "Synergistic action of cholera toxin B subunit (and *Escherichia coli* heat–labile toxin B subunit) and a trace amount of cholera whole toxin as an adjuvant for nasal influenza vaccine," *Vaccine* 12:419–426 (1994).

Tamura et al., "*Escherichia coli* heat–labile enterotoxin B subunits supplemented with a trace amount of the holotoxin as an adjuvant for nasal influenza vaccine," *Vaccine* 12:1083–1089 (1994).

Davenport et al., "Comparisons of serologic and febrile responses in humans to vaccination with influenza A viruses or their hemagglutinins," *J. Lab. & Clin. Med.* 63:5–13 (1964).

Clancy, "Mucosal Vaccines for the Prevention of Influenza," *Drugs* 50:587–594 (1995).

Katz et al., "Adjuvant Activity of the Heat–Labile Enterotoxin from Enterotoxigenic Escherichia coli for Oral Administration of Inactivated Influenza Virus Vaccine," *J. Infect. Dis.* 175:352–363 (1997).

Vieira et al., "The pUC plasmids, an M13mp7–derived system for insertion mutagenesis and sequencing with synthetic universal primers," *Gene* 19:259–268 (1982).

De Haan et al., "Mucosal immunogenicity of the *Escherichia coli* heat–labile enterotoxin: role of the A subunit," *Vaccine* 14:260–266 (1996).

Dallas et al., "Cistrons Encoding *Escherichia coli* Heat–Labile Toxin," *J. Bacteriol.* 139:850–858 (1979).

Van der Linden et al., "Cytoplasmic high–level expression of a soluble, enzymatically active form of the *Escherichia coli* penicillin–binding protein 5 and purification by dye chromatography," *Eur. J. Biochem.* 204:197–202 (1992).

Uesaka et al., "Simple method of purication of *Escherichia coli* heat–labile enterotoxin and chloera toxin using immobilized galactose," *Microb. Path.* 16:71–76 (1994).

Chaloupka et al., "Comparative Analysis of Six European Influenza Vaccines," *Eur. J. Microbiol. Infect. Dis.* 15:121–127 (1996).

Wood et al., "An Improved single–radial–immunodiffusion technique for the assay of influenza haemagglutinin antigen: application for potency determinations of inactivated whole virus and subunit vaccines," *J. Biol. Stand.* 5:237–247 (1977).

Hashigucci et al., "Antibody responses in volunteers induced by nasal influenza vaccine combined with *Escherichia coli* heat–labile enterotoxin B subunit containing a trace amount of the holotoxin," *Vaccine* 14:113–119 (1996).

Nashar et al., "Current progress in the development of the B subunits of cholera toxin and *Escherichia coli* heat–liable enterotoxin as carriers for the oral delivery of heterologous antigens and epitopes," *Vaccine* 11:235–240 (1993).

Verweij et al., "Musosal immunoadjuvant activity of recombinant *Escherichia coli* heat–labile enterotoxin and its B subunit: Induction of systemic IgG and secretory IgA responses in mice by intranasal immunization with influenza virus surface antigen," *Vaccine* 16:2069–2076 (1998).

* cited by examiner

VACCINES WITH AN LTB ADJUVANT

The present invention relates to a vaccine containing the B subunits of heat-labile enterotoxin (LTB) of *Escherdchia coli* (*E. coli*) as a mucosal immunoadjuvant. The invention relates in particular to a vaccine of this type to prevent influenza infections in humans. However, the invention is not restricted to application in influenza vaccines.

It is the object of vaccination against infectious diseases to prevent or at least restrain infection of the vaccinated subject by stimulating an immune response against the Infectious agent through introduction of an antigen formulation derived from the particular pathogen. Ideally, the induced immune response should consist of two components, a humoral response (the production of antigen-specific antibodies) and a cellular response (the generation of specific cytotoxic T lymphocytes, capable of eliminating cells infected by the pathogen).

Many vaccination procedures involve the administration of a formulation containing inactivated or attenuated whole pathogen. However, for certain pathogens there is a considerable disadvantage to vaccination with whole pathogen, since such preparations, even though they are usually highly immunogenic, may have undesirable side effects. This explains the current trend towards the use of well-defined subunit vaccines or synthetic vaccines, substantially lacking the adverse side effects of the whole infectious agent. However, compared to whole pathogen, subunit vaccines or synthetic vaccines are often not very immunogenic, at least in the absence of an added adjuvant.

Adjuvants are substances or materials administered in conjunction with the antigen so as to stimulate the immune response against that antigen. There is a need for appropriate adjuvants which would boost the immune response against subunit antigens or synthetic antigens without causing undesirable side effects.

Influenza vaccine formulations have contained for a long time, and in some cases still contain, inactivated or attenuated whole virus. Such formulation may have considerable side effects, most notably fever and reactions at the site of injection. Nowadays, vaccination is usually done with a subunit formulation. This subunit vaccine, which causes less side reactions, only contains the two major surface antigens of the virus, the hemagglutinin (HA) and the neuraminidase (NA), in a more or less purified form. In most current vaccine formulations there is no added adjuvant present.

The inactivated or attenuated whole influenza virus vaccine as well as the subunit vaccine are usually administered via a single intramuscular (i.m.) injection. The protection against influenza infection, achieved by either vaccination procedure, is comparatively low, particularly in elderly people. The relatively low efficacy of vaccination against influenza is due in part to the high antigenic variability of the virus. However, there is reason to believe that the protection against influenza infection by vaccination can be improved by stimulation and/or modification of the immune response against the antigen.

In the case of influenza, or in general in cases in which the infection is contracted via the respiratory tract, strategies for improved vaccination efficacy should aim at the generation of not only an adequate T-cell-dependent IgG response in the circulation, but also at a local immune response (secretory IgA) in the lungs and nasal cavity as a first line of defence against invading infectious virus. Furthermore, a cellular immune response (cytotoxic T-cells) might also be important, particularly in restricting the infection. It has been demonstrated that administration of influenza vaccine via i.m. injection (the current route of administration) does not result in a local IgA response in the respiratory tract.

The present invention relates to the surprising finding that the presence of LTB in an intranasal vaccine formulation not only stimulates the IgG response in the circulation, relative to i.m. immunisation with the adjuvant-free immunogen vaccine, but also generates a local IgA response in the respiratory tract.

The intact heat-labile enterotoxin (LT), and its close relative cholera toxin (CT), are composed of one A subunit and a pentameric ring structure consisting of five identical B subunits. The A subunit has enzymatic, ADP-ribosylation, activity and attributes the toxic activity to the toxins. In the intestinal epithelium the A subunit induces persistent synthesis of second messenger cAMP, resulting in excessive electrolyte and concomitant fluid secretion to the lumen of the gut.

LT and CT are powerful mucosal immunogens. Upon local mucosal administration these molecules give rise to not only induction of a systemic antibody response directed against the toxin, but also to production of locally secreted antibodies, notably secretory IgA (S-IgA). LT and CT are also powerful mucosal immunoadjuvants. That is, when co-administered with an unrelated other immunogen, LT or CT may stimulate the systemic and mucosal antibody response against that immunogen. However, the toxicity of LT and CT has thusfar essentially precluded the use of LT or CT in human vaccine formulations.

In attempts to separate the toxic from the immune-stimulatory activities of LT or CT, detoxified mutants of the toxins, or the unmodified isolated pentameric B subunit (LTB or CTB, respectively), have been examined for their immunoadjuvant activity. Clearly, because the toxic ADP-ribosylation activity of the toxins resides in the A subunit, the presence of even trace amounts of unmodified A subunit or of LT or CT holotoxin in a human vaccine is highly undesirable.

The use of LTB as an adjuvant for influenza antigens has been investigated by Tamura and co-workers (Hirabashi et al.: Vaccine 8: 243–248 [1990]; Kikuta et al.,: Vaccine 8: 595–599 [1990]; Tamura et al. J.: Immunology 3: 981–988 [1992]; Tamura et al.: Vaccine 12: 419–426 [1994]; Tamura et al.: Vaccine 12: 1083–1089 [1994]). In these studies, based on the use of soluble influenza virus hemagglutinin (HA) vaccine, extracted and purified from influenza virus by treatment with Tween/ether according to Davenport et al (J. Lab. & Clin. Med. 63(1): 5–13 [1964], it was established that LTB, free of A subunit, lacks mucosal immunoadjuvant activity when administered intra-nasally in conjunction with the soluble HA antigen to mice. It was further demonstrated that the presence of trace amounts of holotoxin, for example residual holotoxin remaining in B subunit preparations isolated from holotoxin, restores the expression of adjuvant activity of LTB towards the soluble HA antigen. More in particular, when LTB from recombinant sources (and therefore, completely free of even the smallest trace amounts of A subunit) was used, a trace of holotoxin had to be added in order for the LTB to exert mucosal activity upon intra-nasal co-administration with the soluble HA antigen.

Surprisingly, it was found that isolated LTB from recombinant origin and therefore completely free of A subunit, does possess powerful immunoadjuvant activity depending on the nature or presentation form of the intranasally co-administered immunogen.

For example, adjuvant activity towards freely mixed small soluble antigens, such as ovalbumin or the soluble ectodomain of the envelope glycoprotein of human immunodeficiency virus (gp120), is low and often undetectable. On the other hand, it was found that LTB does exert very powerful adjuvant activity towards freely mixed virus aggregated or particulate immunogens. These immunogens include influenza virus subunit antigen and keyhole limpet hemocyanin (KLH).

Accordingly, the present invention is concerned with a vaccine containing at least one particulate immunogen and an adjuvanting amount of LTB completely free of A subunit or toxic LT holotoxin.

As defined herein, "particulate" means any association of viral, bacterial, or fungal antigens characteristic of the respective micro-organisms. More in particular, the term "particulate immunogen" comprises aggregates, clusters, micelles, virosomes, rosettes, virus-like immunogen particles, and the like.

In the vaccine according to the present invention, in particular, LTB prepared from recombinant DNA technology can be utilised. The immunogen or immunogens may be derived from infective agents, such as viruses or bacteria.

Vaccines which apply to the above description were found not only to induce systemic immunoglobulin (e.g. IgG) against the immunogen upon mucosal (e.g. intra nasal) administration, but were also found to induce local secretion of IgA.

This latter property is particularly favourable for immunisation against diseases which are transmitted by mucosal infection with viruses (such as influenza virus, herpes virus, papilloma virus) or bacteria (like Chiamydia, pneumococs), or fungi.

A particular advantage of mucosal administration is the ease of vaccine application, which, furthermore, circumvents potential needlefobia with vaccinees receiving an intramuscular immunisation.

Although, for example in the case of influenza infection, high serum IgG titres are important for preventing systemic spread of the virus and protection of the lungs against infection, local S-IgA antibodies are crucial as a first line of defence for protection of the upper respiratory tract.

It has been reported that mucosal vaccination by i.n. administration of inactivated influenza virus in the absence of a mucosal adjuvant was not successful (Clancy: Drugs 50: 587–594 [1995]; Katz et al.; J. Infect. Dis. 175: 352–369 [1997]), probably because direct administration of an antigen to mucosal tissue will not result in an S-IgA response. Co-administration of a mucosal adjuvant seems to be a prerequisite to induce a local immune response against an immunogen. Remarkably, it was found that by i.n. immunisation according to the present invention the so-called common mucosal immune system is activated which results in secretion of S-IgA not only at the site of application (i.n.) but also in distant mucosal tissues (e.g. in the vaginal mucosal tissue).

Vaccines according to the present invention may contain immunogens of e.g. viral or bacterial origin, such as bacterial antigens, viral subunits (optionally inactivated) split viruses (optionally inactivated) inactivated viruses or bacteria, or attenuated (e.g. cold-adapted) live viruses, in a particulate form.

The LTB used according to the present invention is strictly free of toxic LTA or toxic holotoxin. Preferably, the LTB is prepared by recombinant DNA technology. Free of toxic LTA in the present context means strictly LTA-free.

In the vaccine according to the present invention the LTB can be used freely admixed with the particulate antigen—a covalent coupling between the antigen and the adjuvant can be established, however it is not needed to attain adequate adjuvant effect.

Apart from LTB and one or more immunogens the vaccine according to the present invention may contain an aqueous solvent, in particular a buffer, more in particular PBS (phosphate-buffered saline) as well as a stabiliser (e.g. PEG or methyl cellulose), and or glucose.

The components of the vaccine according to the present invention may be freeze dried or in a liquid form.

The vaccine according to the present invention may be present e.g. in bulk, or in an ampoule, or in a syringe, or in a nebuliser.

The vaccine according to the present invention may be administered by subcutaneous, or intramuscular, or intra-bronchial, or intra-nasal or intra-vaginal application or per os.

EXAMPLE 1

Preparation of Recombinant LTB and Influenza Subunit Antigen

Recombinant LTB

Recombinant LTB genes and recombinant LTB molecules, as mentioned in the present invention, may be derived from genes encoding LT-I molecules from e.g. a porcine or a human source. The porcine LT (pLT) gene was subcloned in the pUC18 vector (Vieira and Messing: Gene 19: 259268 [1982]) using PCR techniques (DeHaan et al.: Vaccine 14: 260–266 [1996]). The EWD299 vector, originally described by Dallas et al. (J. Bacteriol. 139: 850–858 [1979]) was used as a template in the PCR reaction. The primary pLT sequence of this construct was found to be exactly in accordance with the primary pLT sequence as submitted in the EMBL sequence databank, as verified by DNA sequencing. From the pUC18-pLT construct, the pLTB gene was subcloned in the pROFIT expression vector, which contains a temperature inducible λPR promoter(van der Linden et al.: Eur. J. Biochem. 204: 197–202 [1992]).

*E. coli* MC1061 was used as a host strain for the pROFIT plasmid constructs. Bacteria were grown on Lurda-Bertani medium containing 50 μg of kanamycin per ml. induction of pLTB expression was obtained by raising the culture temperature of log-phase MC1061 cultures harboring the pROFIT-LTB vector from 28 to 42 degrees Celsius as described by De Haan et al. (supra). pTLTB, a pKK-derived expression vector (Pharmacia Ltd.) encoding human LTB (i.e. an LTB gene derived from an LT gene isolated from an *E. coli* bacterium enterotoxigenic in humans) was obtained from Tamura and co-workers. DNA sequencing revealed 3 amino acid substitutions in the mature human LTB (hLTB) compared to pLTB (Thr4 to Ser, Glu46 to Ala, and Lys102 to Glu). *E. coli* strain JM101 was used as a host for pTLTB. Bacteria were grown on LB medium containing 100 μg of ampicillin per ml. Induction of hLTB expression was obtained by addition of IPTG to log-phase cultures of JM101 harboring pTLTB to a final concentration of 5 mM.

For purification of pLTB and hLTB, overexpressing bacteria were harvested, and then lysed by sonication. Subsequently, cell debris was removed by ultracentrifugation. Crude cell extracts containg recombinant pLTB or hLTB were then applied to an immobilised D-galactose (Pierce) column. After extensive washing, recombinant purified pLTB or hLTB were obtained by elution with D-galactose as previously described by Uesaka et al. (Microb. Path. 16: 71–76 [1994]). Both recombinant pLTB and hLTB were found to retain optimal GM1-binding properties in a GM1 capture ELISA, as described previously (DeHaan et al.: Vaccine 14: 260–266 [1996]). Column fractions containing purified protein were pooled, dialysed against PBS and stored at 4° C.

Influenza Subunit Antigen

The influenza subunit antigen was prepared from B/Harbin/7/94 virus (B/Harbin) or A/Johannesburg/33/94 (A/Johannesburg) grown on embryonated chicken eggs according to the method described by Bachmayer et al. (Patent specification GB 1 498 261 of Jan. 18, 1978) and by Chaloupka et al. (Eur. J. Microbiol. Infect. Dis. 15: 121–127 [1996]). This method comprises the steps of treatment of the formaldehyde-inactivated viruses with a suitable cationic detergent, separation of the released antigens (hernagglutinin and neuraminidase) from the virus residual core. This method leads to particulate, i.e. micelle-like exposition of the antigens after removal of the detergent.

The potency of the subunit antigen preparations, expressed as μg per ml, was determined in a single-radial diffusion test according to Wood et al. (J. Biol. Stand. 5: 237–241 [1977]).

EXAMPLE 2

Systemic Antibody Response to Influenza Subunit Vaccine

Groups of four mice were immunised i.n. without anaesthesia with 5 μg of influenza subunit antigen derived from either B/Harbin or A/Johannesburg virus prepared according to the method described in EXAMPLE 1. The antigen was given either alone (HA) or together with 2.0 μg of pLTB (pLTB), in all cases in a volume of 20 μl on days 0, 7 and 14. Control mice received the same volume of PBS. Mice were sacrificed on day 28. Serum IgG antibody response was determined in a direct ELISA.

FIG. 1 shows the observed serum IgG antibody responses against HA B/Harbin (solid bars) and HA A/Johannesburg (open bars). Nasal administration of the subunit antigen without adjuvant gave a poor systemic antibody response, whereas supplementation of the subunit antigen with pLTB enhanced the serum antibody response by more than two orders of magnitude. Differences between the responses of mice immunised with B/Harbin and A/Johannesburg were not significant. These results show that non-toxic pLTB is a powerful adjuvant capable of inducing high systemic antibody responses towards i.n. administered influenza subunit antigen.

EXAMPLE 3

Comparison of Systemic Antibody Responses with Human and Porcine LTB

Groups of 4 mice were immunised i.n. without anaesthesia with 5 μg of influenza subunit antigen derived from B/Harbin influenza virus prepared according to the method described in EXAMPLE 1.

The antigen was given either alone (NONE) or together with either 2.0 μg of pLTB (pLTB) or 2.0 μg of hLTB (hLTB), in all cases in a volume of 20 μl on days 0, 7 and 14. Control animals received PBS. Mice were sacrificed on day 21. Serum IgG antibody response was determined in a direct ELISA on day 21.

FIG. 2 shows the observed serum IgG antibody response against HA B/Harbin. Nasal administration of subunit antigen without adjuvant again gave a poor systemic antibody responses, whereas supplementation of subunit antigen with pLTB and with hLTB enhanced the serum antibody response to the same extent by more than two orders of magnitude. The observed differences between pLTB and hLTB treated animals were non-significant

EXAMPLE 4

Induction of Local Mucosal Antibody Response to Influenza Subunit Vaccine

In order to investigate the ability of pLTB to evoke influenza HA-specific S-IgA responses, nasal washes of the mice from EXAMPLE 2 were analysed for the presence of influenza-specific IgA antibodies. Nasal washes were obtained by flushing 0.5 ml of PBS retrograde via the nasopharynx to the upper part of the trachea, flushing back, and collecting the lavage fluid at the nostrils.

The results are shown in FIG. 3.

The data show that recombinant pLTB induced strong local S-IgA responses against HA. The two different influenza subunit antigens gave similar results.

EXAMPLE 5

Comparison of Mucosal Antibody Responses with Human and Porcine LTB

In order to compare the capacities of pLTB and hLTB to enhance nasal HA-specific antibody responses, nasal washes of the mice from EXAMPLE 3 were taken as described above and analyzed for the presence of HA-specific S-IgA on day 21. FIG. 4 shows that both pLTB and hLTB induced brisk nasal HA-specific antibody responses. Moreover, the responses obtained with pLTB and hLTB were comparable in magnitude, demonstrating that both molecules have comparable adjuvant properties.

EXAMPLE 6

Induction of Genital Mucosal Antibody Response to Influenza Subunit Vaccine Applied I.N.

Figure 1:
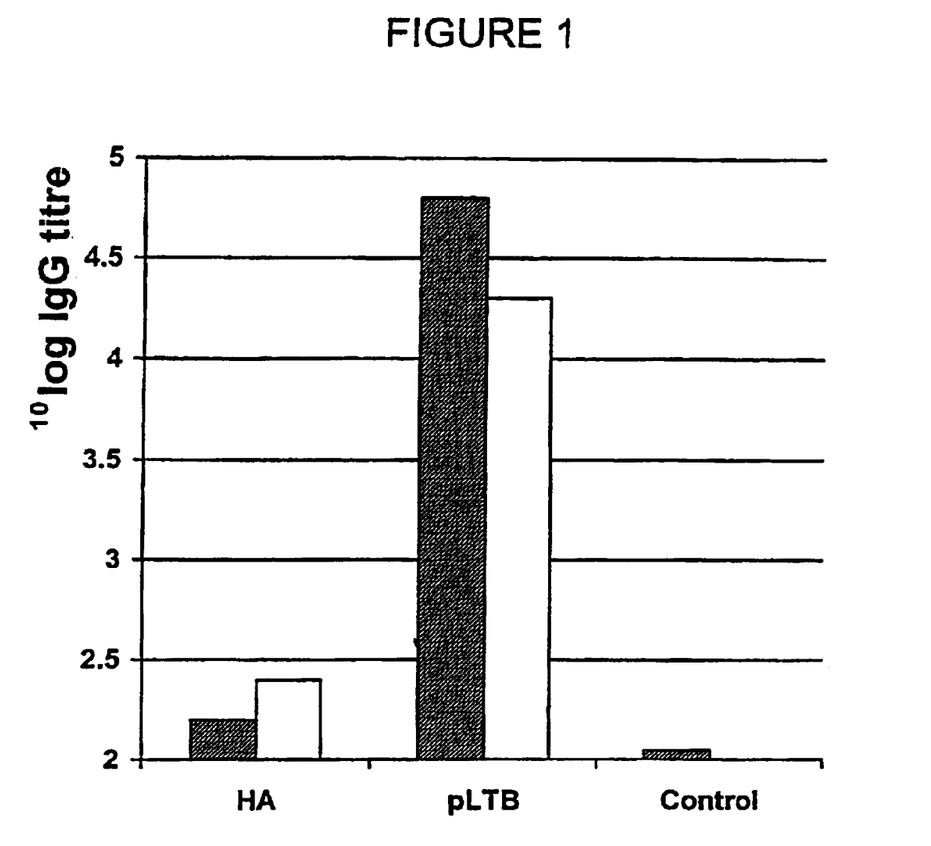
FIG. 1—Observed serum IgG antibody responses against HA B/Harbin (solid bars) and HA A/Johannesburg (open bars), Control: PBS teatrnent; HA: antigen given alone; pLTB: antigen given together with pLTB.
Figure 2:
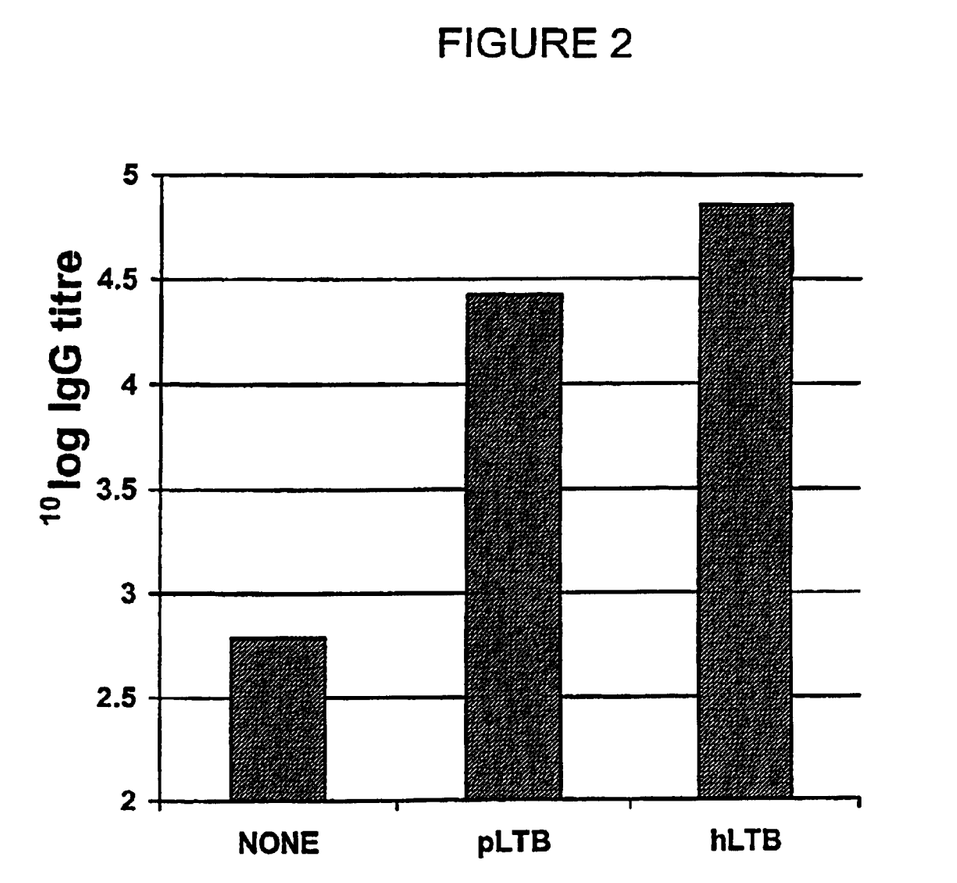
FIG. 2—Observed serum IgG antibody responses against HA B/Harbin. NONE: antigen given alone; pLTB: antigen given together with pLTB; hLTB: antigen given together with hLTB.
Figure 3:
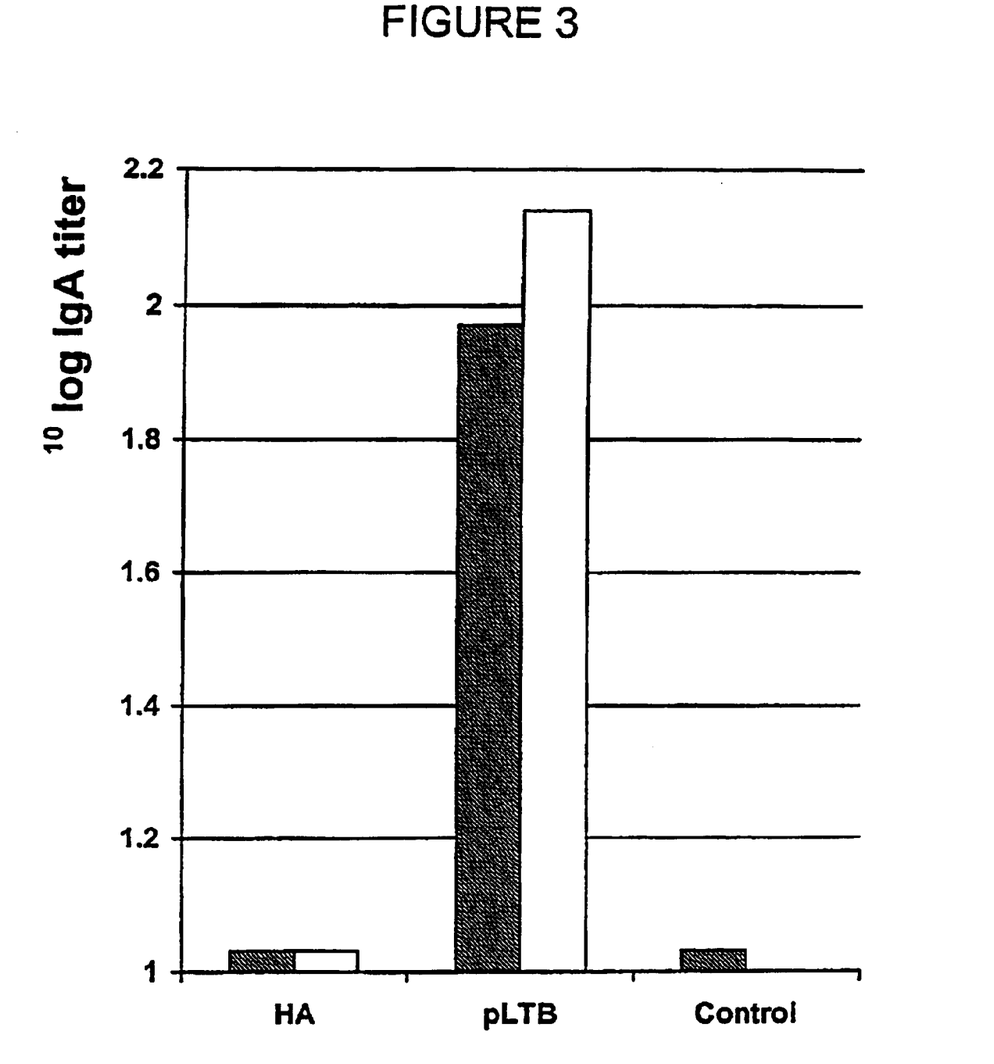
FIG. 3—Observed nasal influenza-specific IgA antibody responses against HA B/Harbin (solid bars) and HA A/Johannesburg (open barns). Control: PBS treatment; HA: antigen given alone; pLTB: antigen given together with pLTB.
Figure 4:
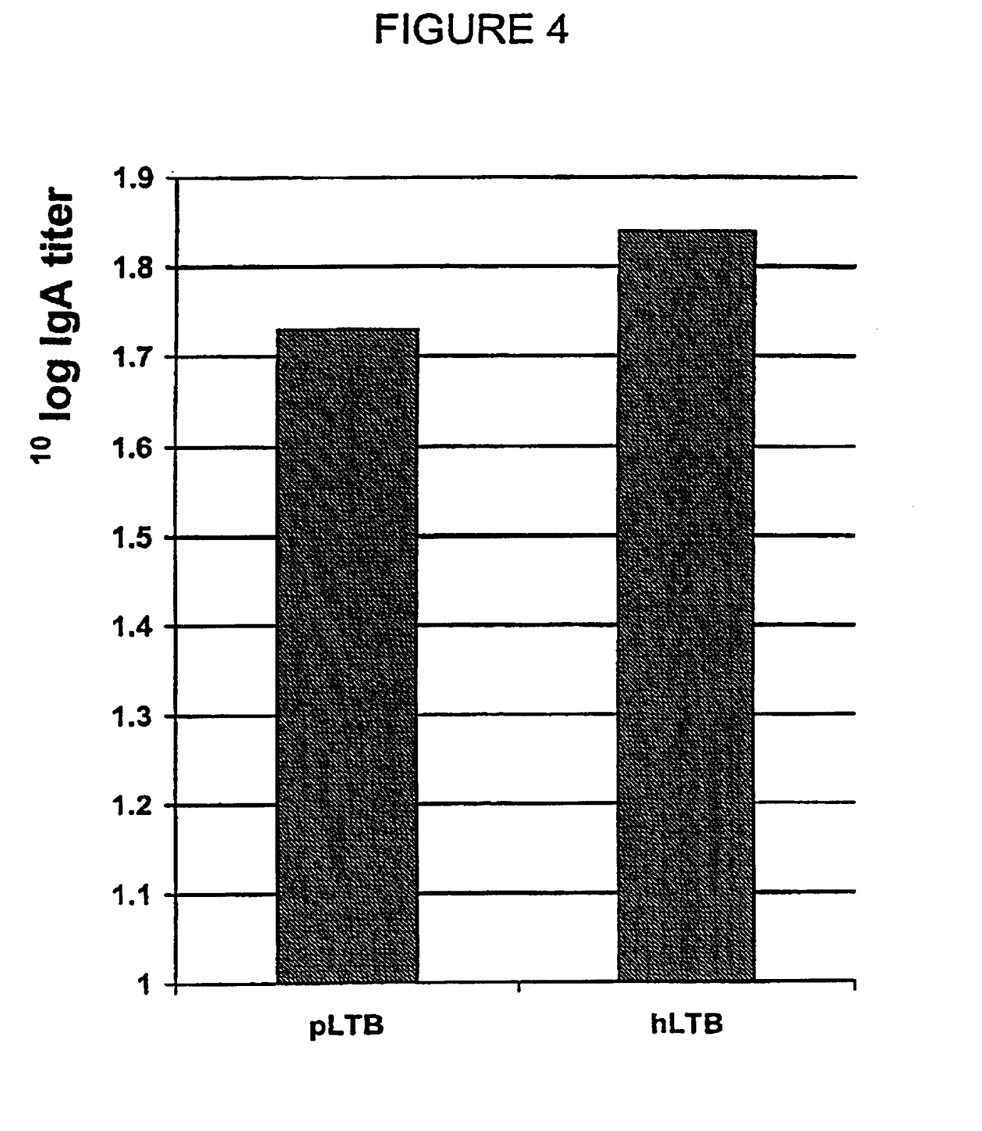
FIG. 4—Observed nasal HA-specific S-IGA antibody responses against HA B/Harbin. pLTB: antigen given together with pLTB; hLTB: antigen given together with hLTB.
Figure 5:
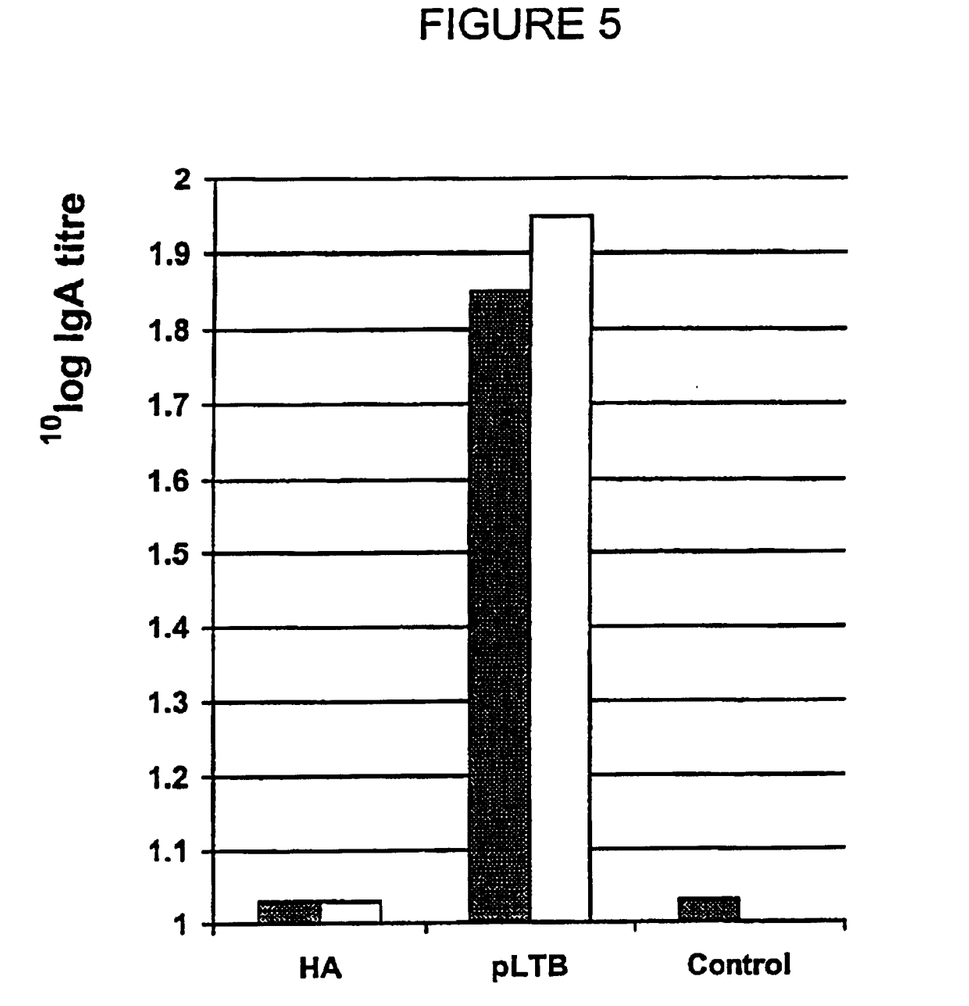
FIG. 5—Observed urogenital HA-specific S-IgA antibody responses against HA B/Harbin (solid bars) and HA A/Johannesburg (open bars), Control: PBS treatment, HA; antigen given alone; pLTB: arifgen given together with pLTB.

In order to investigate the ability of recombinant pLTB to evoke influenza HA-specific S-IgA responses at mucosal sites other than the site of administration, the induction of influenza-specific S-IgA antibodies in the genital tract after i.n. immunisation in the mice from EXAMPLE 2 was investigated. Lavages of the urogenital tract were conducted by introducing and withdrawing a 100 µl volume of PBS ten times into the vagina using a pipette tip. Mucosal washes were stored at 4° C. until determination of their IgA content by ELISA. The results are shown in FIG. 5.

The results show that pLTB proved effective in inducing S-IgA responses at this distant mucosal site. Both B/Harbin and A/Johannesburg antigen responded equally well.

EXAMPLE 7

Kinetics of IgG Response

Four groups of eight female BALB/c mice (6–8 weeks) each were treated as follows
Control treated with PBS without antigen. 20 µl i.n. without anaesthesia on days 0, 7 and 14
pLTB 5 µg HA and 2.0 µg recombinant pLTB in 20 µl applied i.n. without anaesthesia on days 0, 7 and 14
HA s.c. 5 g HA in 100 µl applied s.c. without anaesthesia on day 0
Conv. convalescent mice, i.e. mice infected with $10^8$ infective units of PR8 virus, in 20 µl applied i.n. without anaesthesia on day 0

From four mice of each group blood samples were taken from the tail veins on day 6, 13 and 20. Furthermore, on day 28 all mice were sacrificed and bled. In each sample serum IgG was measured by ELISA.

Figure 6:
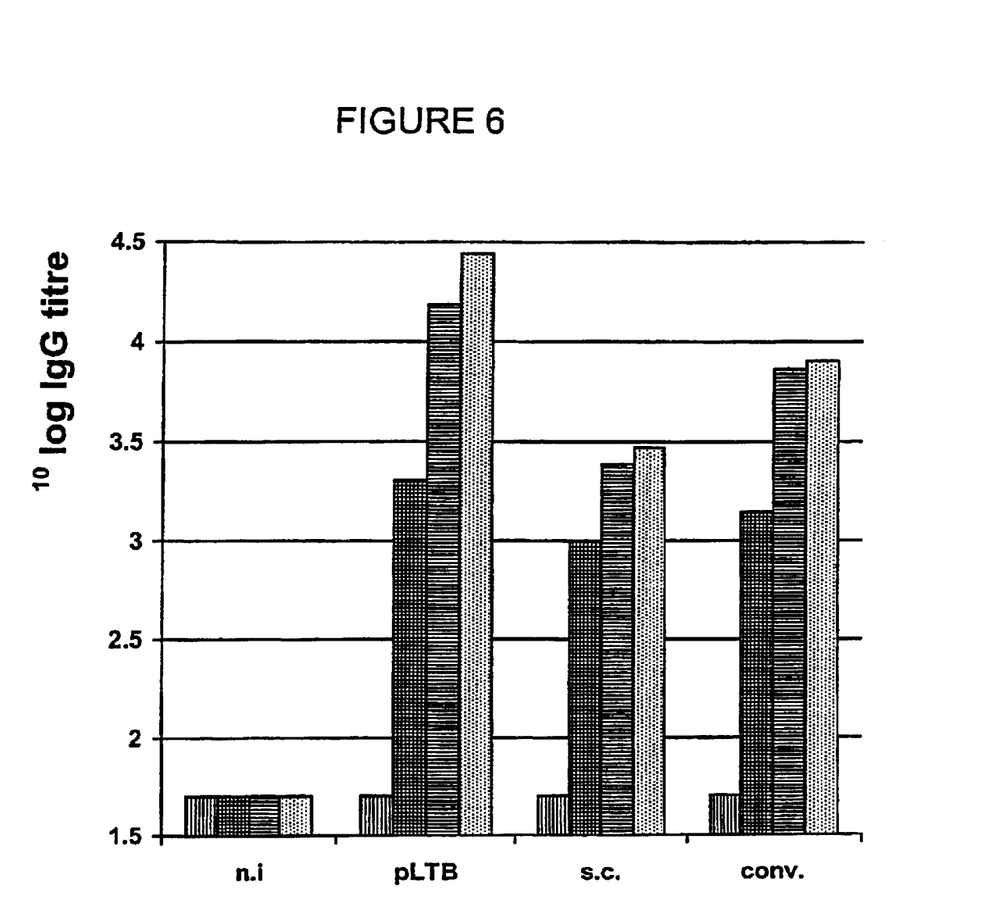
FIG. 6—Observed serum IgG titres on days 6, 13, 20 and 28, respectively (bars from left to right for each of the vaccination regimes), n.i.: controls treated with PBS; pLTB: HA and recombinant pLTB applied i.n.; s.c.: HA applied s.c.; conv.: convalescent mice.

The results are shown in FIG. 6. The bars (from left to right) for each of the vaccination regimens represent the IgG titres on days 6, 13, 20 and 28, respectively. These results show that after i.n. vaccination with HA/pLTB the IgG induction is of at least the same magnitude as after s.c. vaccination with HA alone, or as in convalescent mice.

EXAMPLE 8

Nasal and Lung Mucosal Antibodies

The same mice which were studied in EXAMPLE 7 underwent mucosal lavages of the nasal cavity and the urogenital tract after being sacrificed on day 28 as described above.

Figure 8:
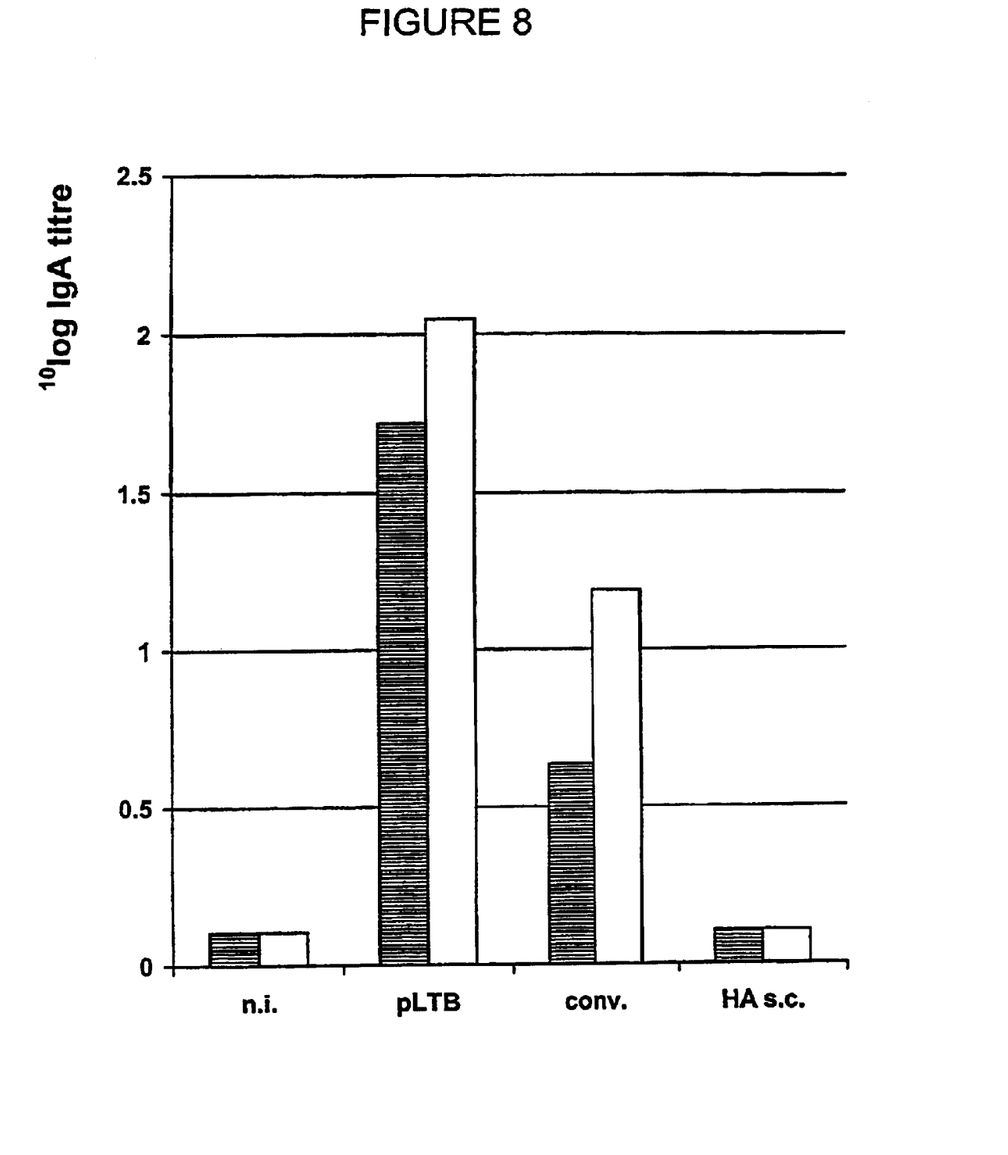
FIG. 8—Observed nasal (hatched bars) and vaginal (open bars) IgA antibody responses. n.i.: controls treated with PBS; pLTB: HA and recombinant pLTB applied i.n.; conv.: convalescent mice; HA s.c.: HA applied s.c.

The results are summarised in FIG. 8. The hatched bars represent the data from nasal washes and the open bars show the data from vaginal washes.

The results indicate that the titre of the first line of defence antibodies (S-IgA) upon i.n. vaccination with HA/pLTB is of at least the same magnitude as the S-IgA titre in convalescent mice whereas the (classical) s.c. vaccination with HA does not lead to a detectable mucosal IgA titre.

EXAMPLE 9

Protection of Vaccinated Mice Against Challenge

Four mice of each of the groups of EXAMPLE 7 were infected on day 28 with $5 \times 10^6$ infective units of PR8 virus i.n. in 20 µl without anaesthesia. Three days post-challenge virus load was determined in nose and lungs.

Virus titration in nose and lung homogenates was carried out on MDCK cells which were cultured on EPISERF cell culture medium (Life Technologies, PAISLY, Scotland) in microtitration plates by two-step dilutions, and by subsequent endpoint determination using haemagglutination with guinea pig erythrocytes.

Figure 7:
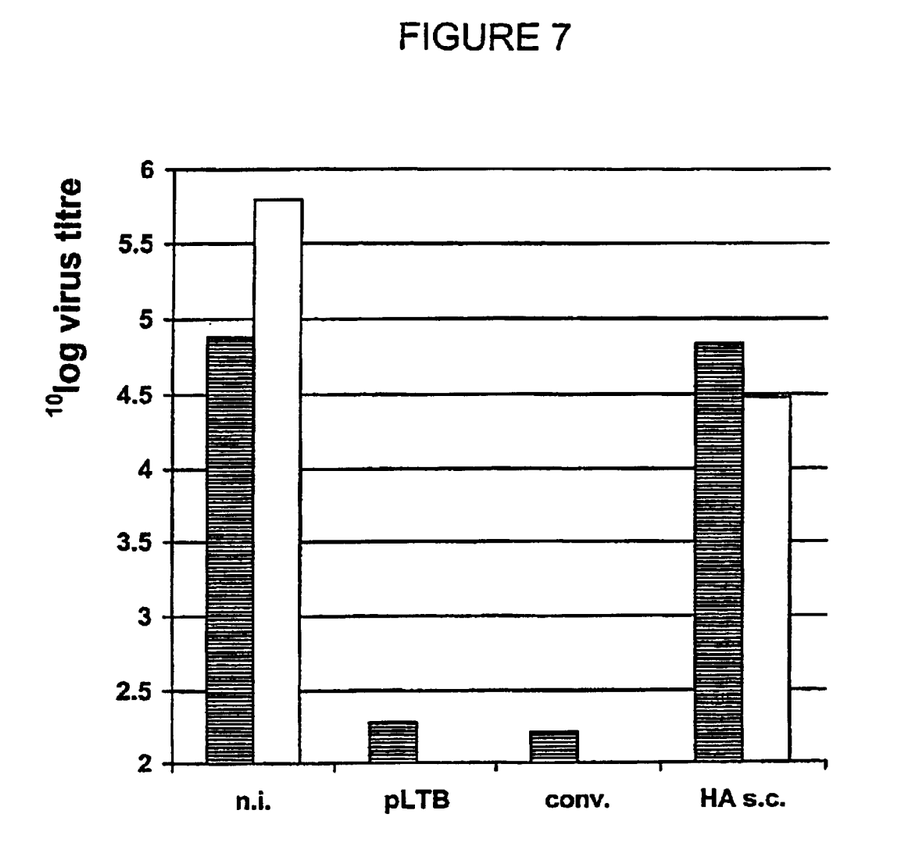
FIG. 7—Post-challenge virus load in nose (hatched bars) and lungs (open bars). n.i.: controls treated with PBS; pLTB; HA and recombinant pLTB applied i.n.; conv.: convalescent mice; HA s.c.: HA applied s.c.

The results are summarised in FIG. 7. The hatched bars represent the virus titres in the nose and the open bars are for the lungs. The virus titres in the lungs for convalescent mice and upon vaccination with pLTB were insignificant. Hence, these data show that by using pLTB as a mucosal adjuvant, protection against influenza infection is complete.

What is claimed is:

1. A vaccine composition comprising at least one immunogen and an adjuvanting amount of B subunits of heat-labile enterotoxin of *E. coil*, wherein said B subunits are free of A subunit and toxic LT holotoxin, wherein said at least one immunogen is not covalently coupled to said B subunits, and wherein said at least one immunogen is in the form of aggregates, clusters, micelles, virosomes, or rosettes, or a mixture of two or more of the foregoing.

2. The vaccine composition according to claim 1, wherein said B subunits are prepared by recombinant DNA methods.

3. The vaccine composition according to claim 1 or claim 2, wherein the at least one immunogen comprises a viral antigen, a bacterial antigen, or a fungal antigen, or a combination thereof.

4. The vaccine composition according to claim 1, wherein the at least one immunogen is from at least one infective agent which causes a disease which is transmitted by mucosal infection.

5. The vaccine composition according to claim 1, wherein the at least one immunogen is from a micro-organism which causes a disease which is transmitted by mucosal infection.

6. The vaccine composition according to claim 1 or claim 2, wherein the at least one immunogen provides immunization against a disease which is transmitted by mucosal infection.

7. The vaccine composition according to claim 6, wherein the at least one immunogen comprises at least one influenza antigen.

8. A method for the induction of a systemic immunoglobulin response against at least one immunogen in a human or animal host in need of such induction, comprising:
administering to mucosal tissue of the host said at least one immunogen in the form of aggregates, clusters, micelles, virosomes, or rosettes, or a mixture of two or more of the foregoing, and an adjuvanting amount of B subunits of heat-labile enterotoxin of *E. coli*, wherein said B subunits are free of A subunit and toxic LT holotoxin, wherein said at least one immunogen together with said B subunits is present in sufficient quantity for said induction, and wherein said at least one immunogen is not covalently coupled to said B subunits.

9. A method for activating the common mucosal immune system against at least one immunogen in a human or animal host in need of such activating, comprising:
administering to mucosal tissue of the host said at least one immunogen in the form of aggregates, clusters, micelles, virosomes, or rosettes, or a mixture of two or more of the foregoing, and an adjuvanting amount of B subunits of heat-labile enterotoxin of *E. coli*, wherein said B subunits are free of A subunit and toxic LT holotoxin, wherein said at least one immunogen together with said B subunits is present in sufficient quantity for said activating, and wherein said at least one immunogen is not covalently coupled to said B subunits.

10. A method of preparing a vaccine for the induction of a systemic immunoglobulin response against at least one immunogen in a human or animal host upon mucosal administration of said vaccine, comprising:

combining said at least one immunogen in the form of aggregates, clusters, micelles, virosomes, or rosettes, or a mixture of two or more of the foregoing, and an adjuvanting amount of B subunits of heat-labile enterotoxin of *E. coli*, wherein said B subunits are free of A subunit and toxic LT holotoxin, wherein said at least one immunogen together with said B subunits is present in sufficient quantity for said induction, and wherein said at least one immunogen is not covalently coupled to said B subunits.

11. A method of preparing a vaccine for activating the common mucosal immune system against at least one immunogen in a human or animal host upon local mucosal administration of said vaccine, comprising:

combining said at least one immunogen in the form of aggregates, clusters, micelles, virosomes, or rosettes, or a mixture of two or more of the foregoing, and an adjuvanting amount of B subunits of heat-labile enterotoxin of *E. coli*, wherein said B subunits are free of A subunit and toxic LT holotoxin, wherein said at least one immunogen together with said B subunits is present in sufficient quantity for said activating, and wherein said at least one immunogen is not covalently coupled to said B subunits.

12. A vaccine comprising at least one immunogen and an adjuvanting amount of B subunits of enterotoxin, wherein said B subunits are free of A subunit and toxic LT holotoxin, wherein said at least one immunogen is not covalently coupled to said B subunits, and wherein said at least one immunogen is in the form of aggregates, clusters, micelles, virosomes, or rosettes, or a mixture of two or more of the forgoing.

13. A vaccine comprising at least one immunogen and an adjuvanting amount of B subunits of cholera toxin, wherein said B subunits are free of A subunit and toxic CT holotoxin, wherein said at least one immunogen is not covalently coupled to said B subunits, and wherein said at least one immunogen is in the form of aggregates, clusters, micelles, virosomes, or rosettes, or a mixture of two or more of the foregoing.

14. A vaccine comprising at least one immunogen and an adjuvanting amount of B subunits chosen from enterotoxin and cholera toxin, wherein said B subunits are free of A subunit, toxic LT holotoxin, and toxic CT holotoxin, wherein said at least one immunogen is not covalently coupled to said B subunits, and wherein said at least one immunogen is in the form of aggregates, clusters, micelles, virosomes, or rosettes, or a mixture of two or more of the foregoing.

15. The vaccine according to claim 12, wherein the at least one immunogen comprises at least one influenza antigen.

16. The vaccine according to claim 13, wherein the at least one immunogen comprises at least one influenza antigen.

17. The vaccine according to claim 14, wherein the at least one immunogen comprises at least one influenza antigen.

18. The vaccine composition of claim 1, wherein the at least one immunogen comprises micelles, rosettes, or a mixture of micelles and rosettes.

19. The vaccine of any one of claim 12, claim 13, and claim 14, wherein the at least one immunogen comprises micelles, rosettes, or a mixture of micelles and rosettes.

* * * * *